United States Patent [19]

Collins

[11] 4,399,687

[45] Aug. 23, 1983

[54] APPARATUS FOR ANALYZING AND IDENTIFYING ODORANTS

[76] Inventor: Carter Collins, 2232 Webster St., San Francisco, Calif. 94115

[21] Appl. No.: 220,001

[22] Filed: Dec. 23, 1980

[51] Int. Cl.³ .......................................... G01N 31/06
[52] U.S. Cl. ....................................... 73/23; 73/27 R
[58] Field of Search ................... 73/23, 27 R, 864.23, 73/864.81, 864.82, 864.83; 422/97, 98

[56] References Cited

U.S. PATENT DOCUMENTS 2,837,912  6/1958  Moncrieff ............................. 73/23

FOREIGN PATENT DOCUMENTS

| 270335 | 8/1970 | U.S.S.R. ............................. 73/27 R |
| 3,549,329 | 12/70 | Silverman et al. ..................... 73/23 |
| 3,578,409 | 5/71 | Silverman et al. ..................... 73/23 |
| 3,610,023 | 10/1971 | Ageikin ............................. 73/27 R |
| 3,751,968 | 8/73 | Loh et al. ............................. 73/23 |
| 3,699,803 | 10/72 | Sumi et al. ......................... 73/27 R |
| 3,756,069 | 9/1973 | Carswell Jr. et al. ............ 73/27 R |
| 3,831,432 | 8/74 | Cox ....................................... 73/23 |
| 3,882,713 | 5/1975 | Nishida et al. ....................... 73/23 |
| 3,932,807 | 1/76 | Wilson ................................. 73/23 |
| 4,013,260 | 3/77 | McClatchas et al. ........... 250/343 |
| 4,092,119 | 5/78 | Baier et al. ....................... 73/27 R |
| 4,164,862 | 8/79 | Jackson 73 ....................... 73/27 |

OTHER PUBLICATIONS

Moncrieff, An Instrument for Measuring and Classifying Odors, J. Appl. Physiol., 1961, 16, 742–749.

Primary Examiner—Stephen A. Kreitman
Attorney, Agent, or Firm—Harris Zimmerman; Howard Cohen

[57] ABSTRACT

An apparatus for analyzing and identifying odorant materials includes a plurality of paired thermistors disposed in a tubular chamber. One of each pair of thermistors is coated with one of a number of adsorbing coatings. Each pair of thermistors is electrically connected to form opposite arms of one of a plurality of Wheatstone bridge circuits. A gas sample carrying a vaporized odorant material is drawn by vacuum induction through the tubular chamber. The odorant material is adsorbed to varying degrees by the coated thermistors, depositing latent heat of vaporization on the coated thermistors and increasing the temperatures and resistances thereof. The uncoated thermistor of each pair acts as a stable temperature reference, and the changes in resistance of the coated thermistor disrupts the balance of the bridge circuit. The peak (or mean) values of the signals resulting from the unbalanced bridge circuits are proportional to the degree of adsorption of the various coatings; the adsorption ratios of each of the coatings results in a unique description (signature) of each odorant sampled; this information can be correlated with data from known odorants to identify a wide spectrum of odorant materials.

11 Claims, 4 Drawing Figures

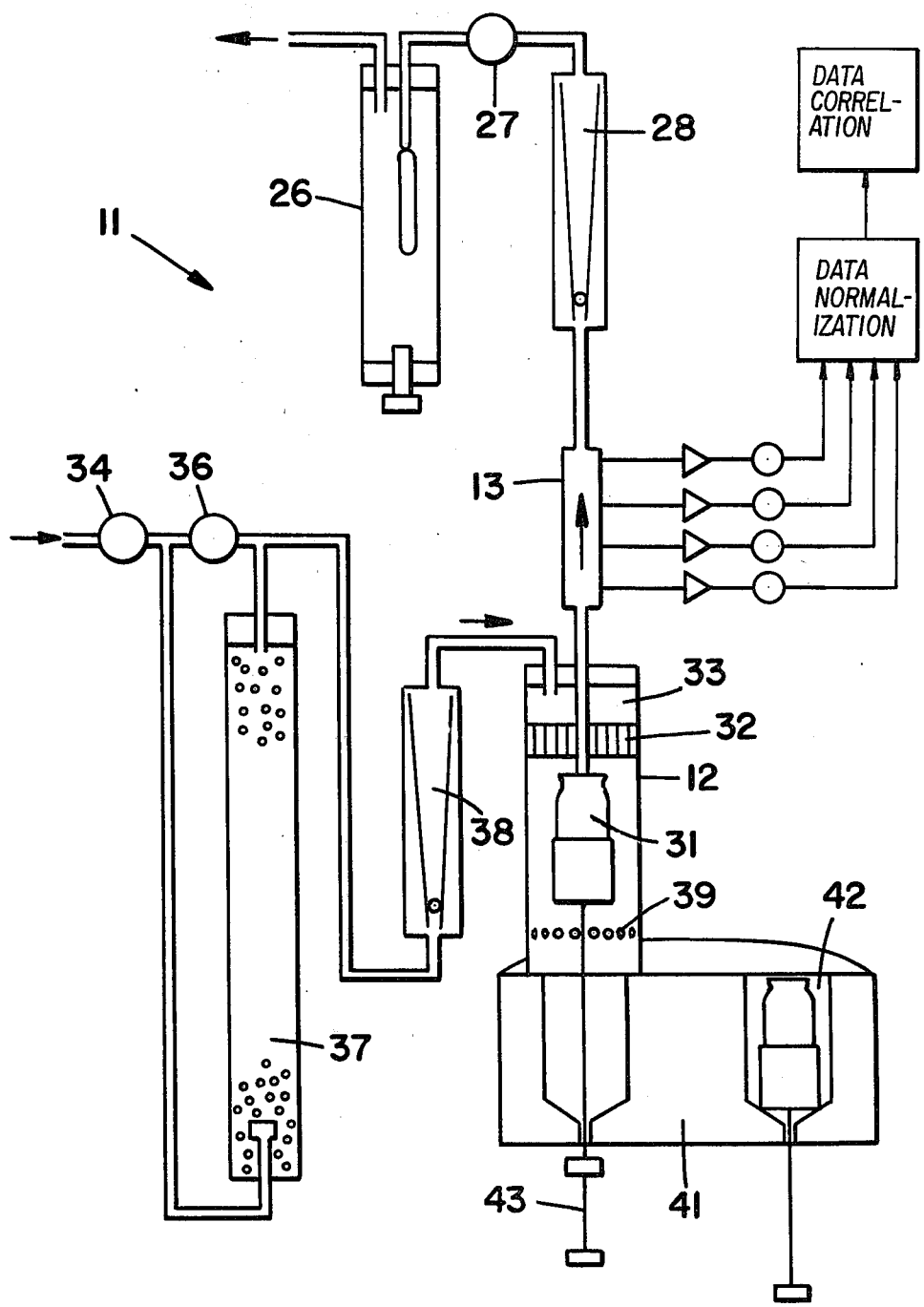
FIG_1

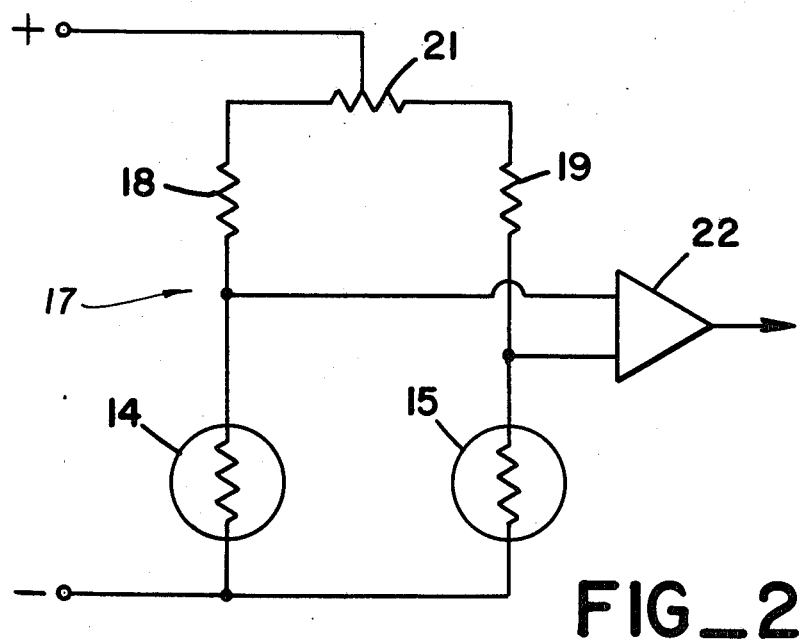
FIG_2
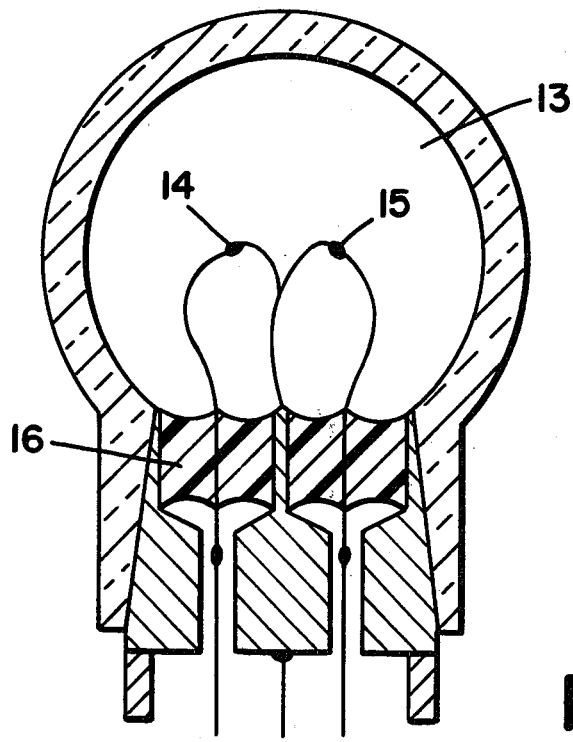
FIG_3

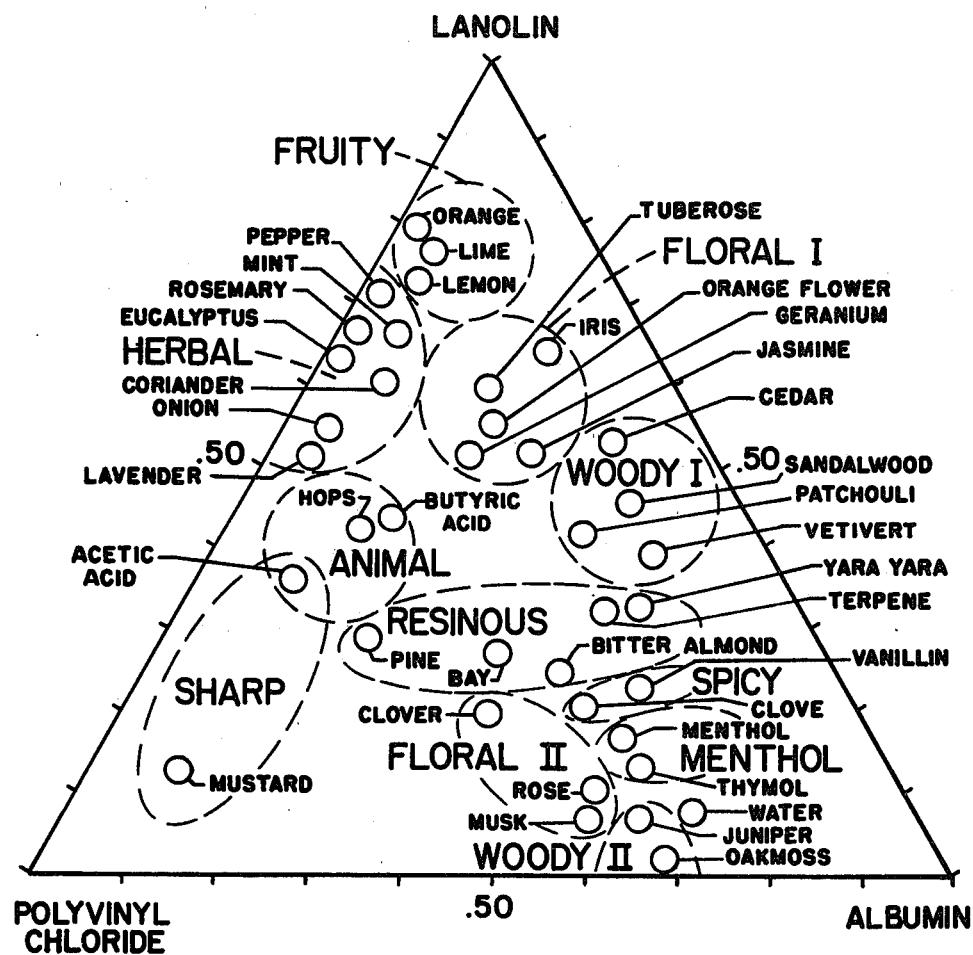
FIG_4

APPARATUS FOR ANALYZING AND IDENTIFYING ODORANTS

BACKGROUND OF THE PRESENT INVENTION

Of all the human senses, the sense of smell is perhaps the most arcane. Although the olfactory sense is capable of discerning extremely minute quantities of airborne odorants, olfactory sensitivity varies widely in any test population and is also quite variable in any one individual. Although there are devices known in the prior art for detecting specific airborne substances, there is no apparatus known in the prior art which is capable of detecting and identifying, particularly in real time, the wide spectrum of odorant materials to which the biological olfactory mechanism is sensitive, or of classifying odorants into categories similar to those perceived and described by man.

There are many potential commercial uses for a device which can detect and identify odorant substances reliably and repeatably. For example, objective odor determination could be used advantageously in the food processing industries, where the freshness and the quality of comestible products could be determined and unpleasing odors or incipient spoilage could be detected objectively through mechanical olfaction. An olfactory device could also have many applications in bringing some objectivity to the judgment of taste of comestible products. Likewise, there would be many uses for such a device in the perfume and cosmetic industries, for analyzing raw materials as well as odor matching products. Olfactory devices could also be employed advantageously in air pollution analyzing equipment, as well as in testing for alcoholic or other drug intoxication.

These commercial applications await the development of an apparatus which can reliably and repeatably emulate the range, sensitivity, and discriminability of biological olfaction.

SUMMARY OF THE PRESENT INVENTION

The present invention generally comprises an apparatus for detecting, analyzing, and identifying a wide range of odorant substances. The apparatus is characterized by its range and sensitivity, which are comparable to the average human olfactory sense. The apparatus is capable of repeatably and reliably identifying minute concentrations of odorant substances.

The apparatus of the present invention includes a chamber through which a gas flow is drawn by vacuum induction. The gas flowing through the chamber carries minute amounts of known or unknown odorant substances. Within the chamber there are disposed a plurality of paired thermistors, each pair forming opposite arms of a Wheatstone bridge circuit. One of each pair of thermistors is coated with a thin layer of a material which adsorbs odorant substances to some extent.

In the absence of any odorant in the flowing gas, each pair of thermistors is maintained at the same tamperature as the flowing gas, and the bridge circuit is balanced. However, adsorption on the coated surface of a thermistor will impart the latent heat of fusion (condensation) of the odorant substance to the coating material and its associated thermistor. As a result, the coated thermistor will undergo a very slight rise in temperature, decreasing the resistance of the thermistor and unbalancing the Wheatstone bridge circuit. The magnitude of the resulting signal is an indication of the amount of adsorption which has taken place on the coating.

Differing coating materials are employed with each pair of thermistors, although in general the coating substances which are used represent the general categories of a protein, a fat, and a long chain polymer (emulating a carbohydrate), all constituents of sensory cells. EAch of these substances will adsorb an odorant material to different extents, and the output signals of the corresponding Wheatstone bridge circuits will indicate the extent of adsorption of each substance. As a result, each unique odorant substance will produce a corresponding unique combination of output signals from the Wheatstone bridge circuits. Any unknown odorant may be analyzed by recording the detector signals which the odorant substance evokes, and correlating those signals and their ratios with previously recorded signal data concerning known odorant substances. This correlation can be accomplished on a real time basis, using microcomputer technology, so that the apparatus may accurately identify odors virtually instantaneously (as does the nose).

A BRIEF DESCRIPTION OF THE DRAWING

FIG. 1 is a schematic view of the olfactory sensing apparatus of the present invention.

FIG. 2 is a schematic diagram of a single olfactory sensor circuit of the apparatus of the present invention.

FIG. 3 is a cross-sectional view of a thermistor pair disposed in the sensing chamber of the present invention.

FIG. 4 is an objective odor discrimination plot of data obtained by the preferred embodiment of the present invention and relating to various odorant substances.

DESCRIPTION OF THE PREFERRED EMBODIMENT

The present invention generally comprises an apparatus for detecting, analyzing, and identifying on a real-time basis a wide variety of odorant substances. With reference to FIG. 1, the preferred embodiment of the apparatus 11 includes a hollow tubular detection chamber 13. The detection chamber 13 is connected in open flow communication to a sample chamber 12 directly adjacent thereto. The detection chamber is adapted to receive a charge of odorant bearing gas from the sample chamber 12. (The sample chamber 12 is a laboratory convenience and not necessary for field sampling.)

Within the detection chamber 13, there is provided a plurality of paired thermistors 14 and 15, as shown in FIGS. 2 and 3. The paired thermistors 14 and 15 are closely longitudinally spaced within the chamber 13, and are positioned to be bathed in the charge of odorant bearing gas delivered from the sample chamber. Preferably, each pair of thermistors is matched so that the paired thermistors do not differ in resistance by more than one-half of one percent. In the preferred embodiment at least three pairs of thermistors are employed, although the invention is not limited to this number of pairs.

One thermistor 14 of each pair is coated with a very thin layer of adsorbing material, while the other thermistor 15 of the pair remains uncoated as a temperature compensating reference. In the preferred embodiment, the coating materials are drawn from the general categories of protein, fat, and polymer, but are not limited to these materials. The substrates chosen from these categories for the preferred embodiment comprise egg albumin, lanolin, and polyvinyl chloride, respectively. The thickness of the coatings is approximately two thousand Angstrom units, and the exposed adsorbing surface area of each coated thermistor is approximately 0.75 square milimeters.

The thermistor leads extend through a sealing plug 16, and are connected to a Wheatstone bridge circuit 17 shown in FIG. 2. The Wheatstone bridge circuit is formed by the paired thermistors 14 and 15 connected at like ends to ground, the other ends of the thermistors being connected to a pair of matched resistors 18 and 19. The other ends of the resistors 18 and 19 are connected to opposite ends of a potentiometer 21, which in turn is connected to a voltage source. A differential amplifier 22 is connected between the ungrounded leads of the thermistors.

As is known in the prior art, the Wheatstone bridge circuit is balanced by means of the potentiometer 21 so that there is no potential difference across the detecting amplifier 22, and hence no output signal from the detecting amplifier. This balanced condition will remain as long as the resistance values of the thermistors 14 and 15 and the resistors 18 and 19 remain unchanged. The resistances 18 and 19 are invariant, so that any changes in the balance condition of the bridge circuit must be due to resistance changes in the thermistors 14 and 15.

The paired thermistors are bathed in the same gas flow, and thus are maintained at approximately the same temperature as the gas flowing through the detection chamber. Thus fluctuations in the resistances of the thermistors due to variations in the temperature of the gas are self-balancing. However, the coating on one of each of the pairs of thermistors 14 will tend to adsorb a small amount of odorant substances carried in the gas flowing thereby. As the odorant substance is adsorbed on one of the coating layers, the latent heat of fusion of the adsorbed odorant molecules is transferred to the coating layer and thus to the thermistor itself. As a result, adsorption of very minute amounts of odorant substances will cause the respective thermistor to undergo a minute temperature increase. The temperature increase in the coated thermistor causes a decrease in the resistance thereof. The changing resistance alters the null or balance condition of the bridge circuit, and results in an output signal from the detecting amplifier 22. The mean or peak value of the signal from the amplifier 22 is proportional to the amount of adsorption taking place on the coated thermistor.

It has been found through experimentation that in a wide range of odorant substances, each odorant substance is adsorbed to differing extents on the coatings of the thermistors, and that the combination of these adsorbing characteristics (their ratios) is unique for each odorant substance. Thus, the signals derived from the detector amplifiers can be used to identify the unique combination of adsorbing characteristics, and to correlate these characteristics with a particular odorant substance, thus identifying in.

For example, the mean or peak values of the signals from three thermistor detector circuits, each coated separately with lanolin, polyvinyl chloride, or albumin, may be normalized as is known in the prior art and their ratios plotted on a triangular coordinate graph as shown in FIG. 4. This triangular graph, also known as a Maxwellian triangle, plots the readings for each odorant substance in a three sided odor classification space. The very interesting result of this plot is that many odorant substances which are identified as similar by human olfaction tend to be grouped together in the same region of the triangular graph. For example, herbal odors tend to be grouped one a small area of the graph, resinous odors in another, methanol-like odors in still another area, and the like. Floral odors and woody odors tend to be separated into two areas on this graph. The grouping of the data from the present invention into well-defined areas which correspond to similar odors as determined by human olfaction points out the high degree to which the present invention simulates the perceptions of the human olfactory sense.

Repeated experimentation has shown that the data obtained for each odorant substance vary by a mean of 3.5% for any one odorant substance, a reliability factor which is estimated to compare with the average human sense of smell. As a result, the placement of the identified areas on the graph of FIG. 4 is definite and accurate to a high degree. Any odorant substance that is tested by the apparatus of the present invention can be identified by plotting the data derived from the unknown sample in the odorant classification space of FIG. 4. If the plotted point falls within the small area of an identified odorant substance, the unknown sample may be identified as the odorant substance. Lacking that correlation, the general area in which the plotted data is located may indicate the general nature of the odorant material; i.e., floral, fruity, woody, or the like.

Indeed, these steps involved in normalizing data and correlating ratios with data from known odorant substances may be performed by electronic computing devices. The response time of the thermistor detector circuit is approximately one second (about that of the nose), and the computational time required for analog to digital conversion, normalization of the data, and correlation of ratios with stored values, also requires about one second. As a result, the apparatus of the present invention can comprise a real-time device for detecting and identifying odorant materials.

Odorant substances may be drawn into the detection chamber 13 by means of a vacuum induction system. As shown in FIG. 1, one end of the tubular detection chamber 13 is connected to a vacuum source by means of a vacuum regulator 26, a flow adjusting valve 27, and a flow meter 28. This arrangement may be used to draw any odorant bearing gas into the direction chamber 13.

In the preferred embodiment, as shown in FIG. 1, the sample chamber 12 is connected directly to the detection chamber 13. Disposed in the upper end of the sample chamber is a laminar flow plate 32 and a plenum chamber 33, both provided to insure laminar flow of gas sweeping downward through the detection chamber. The upper end of the sample chamber is connected to a purging gas supply through a flow adjusting valve 34, a wet-dry selecting valve 36, a water vapor saturation means 37, and a flow meter 38. The valve 36 determines whether the purging gas travels directly through the flow meter into the sample chamber, or first courses through a purified water source to separate the gas with water vapor. Thus the valve 36 selects odorant bearing gas which is either dry or saturated. The purging gas flows into the top of the sample chamber and out of outflow ports 39 in the bottom of the sample chamber.

Directly below the sample chamber there is disposed a rotating airlock 41. The airlock is generally cylindrical, and is provided with at least a pair of receptacles 42 for supporting sample vials 31. The airlock may be rotated about its axis to dispose one of the receptacles 42 in registration with the open bottom of the sample chamber 12. A thin metal rod 43 then extends upwardly through the receptacle to elevate the sample vial out of the receptacle and into the sample chamber. The open end of the sample vial is elevated to be directly adjacent to the intake opening of the detection chamber 13, so that the vacuum induction system may draw a sample of the purging gas and the odorant substance borne thereby into the detection chamber. The samples contained in the vials may comprise any sort of odorant substance to be tested. For example, foodstuffs such as canned goods, coffee, tea, and the like may be placed in the vials and automatically analyzed by the apparatus shown in FIG. 1. Likewise, any perfume, cosmetic, chemical, or the like may be tested for odorant characterstics.

Alternatively, the system may be utilized without a sample chamber 12 and the alternate embodiment may utilize a water saturated fiber (wick or cotton batting) in the line before the detection chamber 13. This arrangement would permit direct field samples to be made of odorants in the atmosphere or material of any kind to be sampled directly by the system. This would simplify the system and permit a small portable (hand-held) device to be utilized by workers sampling odors in the field.

I claim:

1. An apparatus for detecting and identifying odorant substances, comprising: a detection chamber; means for delivering a charge of odorant-bearing gas into said chamber; a plurality of temperature sensing devices disposed in said chamber; a plurality of selectively adsorbing coating means, each disposed on one of a portion of said plurality of temperature sensing devices for adsorbing said odorant substances and utilizing the latent heat of fusion thereof and transferring said latent heat to the respective temperature sensing device; means for detecting a plurality of temperature differences between said portion of said plurality of temperature sensing devices and the remainder of said devices; means for normalizing said plurality of temperature differences with respect to the sum of said temperature differences; and means for correlating said normalized temperature differences with the selective adsorption characteristics of known odorant substances to identify the odorant substances.

2. The apparatus of claim 1, wherein said temperature sensing devices comprise thermistors.

3. The apparatus of claim 2, wherrein said means for detecting temperature differences comprises a plurality of Wheatstone bridge detectors.

4. The apparatus of claim 3, wherein each one of said portion of said devices is paired with one of said remainder of said devices to form adjacent arms of one of said Wheatstone bridge detectors.

5. The apparatus of claim 1, wherein said means for delivering a charge of odorant-bearing gas includes a vacuum induction system connected to said detection chamber.

6. The apparatus of claim 1, wherein said plurality of selectively adsorbing coatings include a fat substance, a protein substance, and a polymer substance.

7. The apparatus of claim 6, wherein said fat substance comprises lanolin.

8. The apparatus of claim 6, wherein said protein substance comprises albumin.

9. The apparatus of claim 6, wherein said polymer substance comprises polyvinyl chloride.

10. The apparatus of claim 1, wherein said means for delivering a charge of odorant bearing gas includes means for adding a substantial amount of water vapor to said gas.

11. The apparatus of claim 1, wherein said means for delivering a charge of odorant bearing gas includes means for removing a substantial proportion of water vapor from said gas.

* * * * *